(12) United States Patent
Moar

(10) Patent No.: US 6,280,722 B1
(45) Date of Patent: Aug. 28, 2001

(54) ANTIFUNGAL *BACILLUS THURINGIENSIS* STRAINS

(75) Inventor: William J. Moar, Auburn, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 09/333,373

(22) Filed: Jun. 15, 1999

Related U.S. Application Data

(63) Continuation-in-part of application No. 08/921,436, filed on Aug. 29, 1997, now abandoned.
(60) Provisional application No. 60/025,108, filed on Aug. 30, 1996.

(51) Int. Cl.[7] .............................. A61K 63/00; C12N 1/20; C12N 1/21
(52) U.S. Cl. ..................................... 424/93.461; 424/93.2; 435/252.31; 435/252.5
(58) Field of Search .............................. 424/93.461, 93.2; 435/252.5, 252.31, 209; 536/23.2, 23.7, 23.71

(56) References Cited

PUBLICATIONS

Smirnoff et al., Determination of the Chitinolytic Activity of Nine Subspecies of *Bacillus Thuringiensis, Journal of Invertebrate Pathology*, 1997, pp. 265–266, vol. 30, Academic Press, Inc.

Sekar et al., Molecular Cloning and Characterization of the Insecticidal Crystal Protein Gene of *Bacillus Thuringiensis* Var. *Tenebrionis,* Proc. Natl., Acad. Sci. USA, Oct. 1987, pp 7036–7040, vol. 84, Biochemistry.

Cody, R.M., Distribution of Chitinase and Chitobiase in Bacillus Current Microbiology, 1989, pp. 201–205, vol. 19, Springer–Verlag New York Inc.

*Primary Examiner*—Mary E. Mosher
(74) *Attorney, Agent, or Firm*—Alston & Bird LLP

(57) ABSTRACT

An improved *Bacillus thuringiensis* biocontrol stain, useful to control insect and fungal attack on crop plants, is provided. The chitinase and DNA sequence encoding the chitinase are also encompassed.

23 Claims, No Drawings

ANTIFUNGAL *BACILLUS THURINGIENSIS* STRAINS

RELATED APPLICATION(S)

This application is a continuation-in-part of U.S. patent application Ser. No. 08/921,436 filed Aug. 29, 1997, now abandoned, which claims the benefit of U.S. Provisional Application No. 60/025,108, filed Aug. 30, 1996.

FIELD OF THE INVENTION

The present invention relates to the identification of a mutant strain of *Bacillus thuringiensis* (Bt) which has improved antifungal activity.

BACKGROUND OF THE INVENTION

Plant diseases reduce both the quantity and quality of plant products. Annual crop losses caused by disease amount to about 15% of expected harvest even in industrialized countries. The causes of plant diseases are many and diverse.

Infectious agents of plant diseases include such different groups as viroids, viruses, mollicutes, rickettsias, bacteria, actinomycetes, fungi, algae, protozoans, nematodes, insects and mites. A large percentage of all plant diseases is caused by fungi. These diseases are often spread by insects.

The soil microbe *Bacillus thuringiensis* (Bt) is a gram-positive, spore-forming bacterium characterized by parasporal crystalline protein inclusions. These inclusions can be observed microscopically as distinctly shaped crystals. The proteins are generally toxic to certain insects and contain specific endotoxic activity. Numerous Bt toxin genes have been isolated, sequenced, and recombinant DNA-based Bt products have been produced and approved for use.

Since the 1950's, formulations of Bt have been used as biological insecticides to control agricultural insect pests and more recently, insect vectors of a variety of human and animal diseases. Preparations of spores and crystals of *B. thuringiensis* var. kurstaki have been used for many years as commercial insecticides for lepidopteran pests.

Aflatoxins are highly carcinogenic compounds that are metabolic products of the ubiquitous fungi, *Aspergillus flavus* and *A. parasiticus*. Aflatoxins can contaminate peanuts and other crops such as corn whenever this commodity is invaded by the fungi. Reduction of aflatoxin contamination is a priority need in the production of peanuts (*Arachis hypogaea*). Aspergillus-like fungi invade peanut tissue when hot, dry weather prevails, especially during the last 4–6 weeks of the growing season. Fungal invasion of the developing peanut seed is facilitated when the pods are damaged in any way, such as feeding damage caused by the soilborne larvae of the lesser cornstalk borer (LCB), *Elasmopalpus lignosellus*, (Lepidoptera: Pyralidae).

Peanut pods and seed develop underground which makes preharvest control of aflatoxin contamination extremely difficult. Fungi that produce aflatoxins survive well in soil and invade developing peanut pods throughout growing season. Because no chemicals are effective against aflatoxin contamination of peanuts and culture control tactics are impractical, alternatives such as biological control are needed.

Organisms exhibiting biological control activity and natural products are among the control alternatives being sought for aflatoxin control. Organisms with biological control activity have an advantage of colonizing and, presumably, increasing in population as control is manifested. Natural products and biological control do not have the same negative impacts on the environment that synthetic pesticides may have. In addition, as synthetic pesticides become more difficult and expensive to discover and register, natural products are becoming increasingly important as alternatives.

One class of "biological control" compounds which have been investigated are the chitinases. Chitinases have been implicated in helping to control both insects and fungi, and also to help degrade crustacean exoskeltons, as they collect after the meat has been harvested from shellfish such as shrimp and crab. As a result, numerous chitinase genes have been cloned and sequenced from bacteria, plants, and actinomycetes. Interestingly, many of these chitinase genes display little sequence homology with other chitinase genes.

Therefore, there is needed biocontrol strains which are effective against insects and fungi.

SUMMARY OF THE INVENTION

A novel *Bacillus thuringiensis* (Bt) strain is disclosed having increased activity against plant pathogenic fungi. The strain retains insecticidal activity against certain lepidopteran plant pests. Further, DNA sequences which encode the chitinase activity of the strain are also encompassed. These chitinase genes encode proteins with potential antifungal and/or insecticidal activity. The invention further discloses the use of the strain and DNA sequences for protection of plants from fungal and insect damage.

DETAILED DESCRIPTION OF THE INVENTION

The present invention provides an improved biocontrol strain of Bt which can be used to control pathogenic attack on crop plants. The strain is able to aggressively control fungal and insect attack. The strain is an enhanced chitinolytic isolate of *Bacillus thuringiensis* subsp. dendrolimus, (HD-548).

The strain produced by mutagenesis and selection shows enhanced fungicidal activity against certain plant pathogenic fungi. Such fungi include: Botrytis, particularly *B. cineria*; Alternaria, particularly *A. solani*; Aspergillus, etc. Additionally the strain retains the insecticidal activity normally attributed with the wild-type, or parent Bt. That is, the Bt strain of the invention protects plants against damage by lesser cornstalk borer and other lepidopteran pests typically susceptible to Cry1Ab and Cry1Ac toxins. The Bt strain is designated AU634 and has been deposited with the USDA NRRL in Peoria, Ill. as NRRL B-21620.

Bt strain AU634 inhibits growth and reduces aflatoxin production by Aspergillus, particularly *A. flavus* and *A. parasiticus* in peanuts. The strain additionally has substantial activity against lesser cornstalk borer. Accordingly, the novel strain finds use as a pesticidal spray or alternatively as a seed treatment.

General methods for employing the strains of the invention in pesticide control or engineering other organisms as pesticidal agents are known in the art. See, for example, U.S. Pat. No. 5,039,523 and EP 0480762A2. Preferred methods of applying active strains of the invention or an agrochemical composition of the present invention are leaf application, seed coating and soil application. The number of applications and the rate of application depend on the intensity of infestation by the corresponding pests and other agronomic factors.

Bt strain AU634 is a result of mutagenesis and selection of Bt strain HD-548 obtained from the USDA NRRL collection in Peoria, Ill., NRRL HD-548. Strain HD-548 was incubated with N-methyl-N'-nitro-N-nitrosoguanidine. Colonies were selected for enhanced chitinase activity with subsequent demonstrated fungicidal activity against *Aspergillus flavus* and *Alternaria solani*. The strain was additionally tested to ensure that lepidopteran activity was not affected.

Fungal invasion of developing peanut seed is facilitated when the pods are damaged in any way. Feeding damage by the soilborne larvae of the lesser cornstalk borer insect, in particular, has been shown to be closely related to peanut seed invasion by *A. Flavus*-type fungi. Peanut seed develop in the soil over an extended period of time. Throughout peanut pod development, seed may become invaded by aflatoxigenic fungi. Thus, strain AU634 is an ideal biocontrol agent, as it prevents seed pod damage by the insect and has antifungal activity.

A general characterization of strain AU634 is as follows: Parent strain is HD-548, serotype 4a:4b, colony morphology: colony edge is rounded and mostly smooth. The isolate can degrade sufficient chitin on a Nutrient agar plant supplemented with 0.4% colloidal chitin plate so that a visible clearing zone can be detected after 36 hours. Exhibits putative antibiosis against *Botrytis cinerea* and *Alternaria solani.*

The present invention is also drawn to a novel chitinase and the DNA sequence encoding the novel chitinase in strain AU634. The chitinase (SEQ. ID NO: 1) comprises an N-terminal sequence as follows:

Ala-Asn-Asn-Leu-Gly-Ser-Glu-Leu-Ileu-Val-Gly-Tyr-Phe-Pro-Asn-Phe-Asp-Asn-Gly-Thr This N-terminal sequence exhibits little homology with any of the published chitinases. For the N-terminal sequence see also SEQ ID NO: 1.

To obtain the DNA sequence encoding the chitinase, DNA probes corresponding to the amino acid sequence can be utilized. Alternatively, to obtain the nucleotide and amino acid sequences of the chitinase protein, other methods available in the art can be utilized. For example, to obtain the nucleotide sequence encoding the chitinase, cosmid clones, which express the protein can be isolated from a genomic library. From larger active cosmid clones, smaller subclones can be made and tested for activity. In this manner, clones which express an active protein can be sequenced to determine the nucleotide sequence of the gene. Then, an amino acid sequence can be deduced for the protein. For general molecular methods, see, for example, *Molecular Cloning, A Laboratory Manual,* 2nd Ed. Vol. 1–3, Sambrook et al. (eds.) Cold Spring Harbor Laboratory Press., Cold Spring Harbor, N.Y. (1989), and the references cited therein.

The present invention also encompasses chitinase sequences from other organisms where the nucleotide sequences are isolatable by hybridization with the chitinase sequences of the invention. Proteins encoded by such nucleotide sequences can be tested for fungicidal and insecticidal activity.

Once the nucleotide sequences encoding the chitinase proteins of the invention have been isolated, they can be manipulated and used to express the protein in a variety of hosts including other organisms, including microorganisms and plants.

If necessary, the genes of the invention can be optimized for enhanced expression in plants. See, for example, EPA 0359472; EPA 0385962; WO 91/16432; Perlak et al. (1991); Proc. Natl. Acad. Sci. USA 88:3324–3328 Perlak et al. (1991) Proc. Natl. Acad. Sci. USA 88:3324–3328; and Murray et al. (1989) Nucleic Acids Research 17: 477–498. In this manner, the genes can be synthesized utilizing plant preferred codons. That is the preferred codon for a particular host is the single codon which most frequently encodes that amino acid in that host. The peanut preferred codon, for example, for a particular amino acid may be derived from known gene sequences from peanut. Synthetic genes can also be made based on the distribution of codons a particular host uses for a particular amino acid.

In this manner, the nucleotide sequences can be optimized for expression in any plant. It is recognized that all or any part of the gene sequence may be optimized or synthetic. That is, fully synthetic or partially optimized sequences may also be used.

In like manner, the nucleotide sequences can be optimized for expression in any microorganism.

Methodologies for the construction of plant expression cassettes as well as the introduction of foreign DNA into plants are described in the art. Such expression cassettes may include promoters, terminators, enhancers, leader sequences, introns and other regulatory sequences operably linked to the chitinase protein coding sequence.

The expression cassette will include the in 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens,* such as the octopine synthase and nopaline synthase termination regions. See also, Guerineau et al., (1991), Mol. Gen. Genet., 262:141–144; Proudfoot, (1991), Cell, 64:671–674; Sanfacon et al., (1991), Genes Dev., 5:141–149; Mogen et al., (1990), Plant Cell, 2:1261–1272; Munroe et al., (1990), Gene, 91:151–158; Ballas et al., (1989), Nucleic Acids Res., 17:7891–7903; Joshi et al., (1987), Nucleic Acid Res., 15:9627–19639).

The construct may also include any other necessary regulators such as plant translational consensus sequences (Joshi, C.P., (1987), Nucleic Acids Research, 15:6643–6653), introns (Luehrsen and Walbot, (1991), Mol. Gen. Genet., 225:81–93) and the like, operably linked to the nucleotide sequence of interest.

It may be beneficial to include 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein, O., Fuerst, T. R., and Moss, B. (1989) PNAS USA 86:6126–6130); potyvirus leaders, for example, TEV leader (Tobacco Etch Virus) (Allison et al., (1986); MDMV leader (Maize Dwarf Mosaic Virus); Virology, 154:9–20), and human immunoglobulin heavy-chain binding protein (BiP), (Macejak, D. G., and Samow, P., (1991), Nature, 353:90–94; untranslated leader from the coat protein mRNA of alfalfa mosaic virus (AMV RNA 4), (Jobling, S. A., and Gehrke, L., (1987), Nature, 325:622–625; tobacco mosaic virus leader (TMV), (Gallie, D. R. et al., (1989), Molecular Biology of RNA, pages 237–256; and maize chlorotic mottle virus leader (MCMV) (Lommel, S.A. et al., (1991), Virology, 81:382–385. See also, Della-Cioppa et al., (1987), Plant Physiology, 84:965–968.

In preparing the expression cassette, the various DNA fragments may be manipulated, so as to provide for the DNA sequences in the proper orientation and, as appropriate in the proper reading frame. Towards this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resection, ligation, or the like may be employed, where insertions, deletions or substitutions, e.g. transitions and transversions, may be involved.

The recombinant DNA molecules of the invention can be introduced into the plant cell in a number of art-recognized ways. Those skilled in the art will appreciate that the choice of method might depend on the type of plant, i.e. monocot or dicot, targeted for transformation. Suitable methods of transforming plant cells include microinjection (Crossway et al. (1986) BioTechniques 4:320–334), electroporation (Riggs et al. (1986) Proc. Natl. Acad. Sci. USA 83:5602–5606, Agrobacterium mediated transformation (Hinchee et al. (1988) Biotechnology 6:915–921), direct gene transfer (Paszkowski et al. (1984) EMBO J. 3:2717–2722), and ballistic particle acceleration (see, for example, Sanford et al., U.S. Pat. No. 4,945,050; and McCabe et al. (1988) Biotechnology 6:923–926). Also see, Weissinger et al. (1988) Annual Rev. Genet. 22:421–477; Sanford et al. (1987) Particulate Science and Technology 5:27–37(onion); Christou et al. (1988) Plant Physiol. 87:671–674(soybean); McCabe et al. (1988) Bio/Technology 6:923–926 (soybean); Datta et al. (1990) Biotechnology 8:736–740(rice); Klein et al. (1988) Proc. Natl. Acad. Sci. USA, 85:4305–4309 (maize); Klein et al. (1988) Biotechnology 6:559–563 (maize); Klein et al. (1988) Plant Physiol. 91:440–444(maize); Fromm et al. (1990) Biotechnology 8:833–839; and Gordon-Kamm et al. (1990) Plant Cell 2:603–618 (maize).

The cells which have been transformed may be grown into plants in accordance with conventional ways. See, for example, McCormick et al., Plant Cell Reports (1986), 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

A variety of ways are available in the art for introducing a gene into a microorganism host under conditions which allow for stable maintenance and expression of the gene. These methods are well known to those skilled in the art and are described, for example, in U.S. Pat. No. 5,135,867, which is incorporated herein by reference.

The cellular host containing the chitinase gene may be grown in any convenient nutrient medium, where the DNA construct provides a selective advantage, providing for a selective medium so that substantially all or all of the cells retain the gene. These cells may then be harvested in accordance with conventional methods. Alternatively, the cells can be treated prior to harvesting.

The Bt cells of the invention can be cultured using standard art media and fermentation techniques. Upon completion of the fermentation cycle the bacteria can be harvested by first separating the Bt spores and crystals from the fermentation broth by means well known in the art. The recovered Bt spores and crystal can be formulated into a wettable powder, liquid concentrate, granules or other formulations by the addition of surfactants, dispersants, inert carriers, and other components to facilitate handling and application for particular target pests. These formulations and application procedures are well known in the art.

The Bt cells of the invention can also be further modified by further mutation or selection methods as well as serving as hosts for the insertion of heterologous genes, such as insecticidal or fungicidal genes. In this manner improved strains can be provided. Such insecticidal and/or fungicidal genes include Bt insecticidal genes, chitinase genes, osmotin genes, lectin genes, protease inhibitor genes, $\beta$ 1–3 glucanase genes, enhancin genes, etc. Thus, the invention encompasses strain AU634 which has been transformed with a gene or genes to broaden and/or increase the fungicidal and/or insecticidal activities of the strain.

As discussed above, the genes for transformation of the Bt strains will be present as part of an expression cassette which is expressed in the Bacillus host. Such an expression cassette will include a promoter or 5' transcriptional initiation region and a termination region functional in the host. The sequence can be synthesized for optimum expression in the Bacillus host by using Bacillus codons. Other modifications as discussed for plant expression may be applicable.

A further embodiment of the invention provides a method for controlling or inhibiting the growth of a plant pathogenetic fungus by applying the biocontrol strains of the invention to the environment in which the plant pathogenic fungus may grow. Such application includes applying the strain to the plant or parts of the plant or seeds (prior to planting) of the plant to be protected, or alternatively to the soil in which the plant to be protected is growing or will grow. The strains will be applied in an effective amount. That is, in an amount sufficient to control or inhibit the pathogen. The rate of application may vary according to the crop to be protected, the advocacy of the biocontrol strain, the pathogen to be controlled, and the severity of the disease pressure. Generally, the rate of application will be about $10^5$/seed to about $10^9$/seed, preferably about $10^6$/seed to about $10^8$/seed, more preferably about $10^6$/seed to about $10^7$/seed for protection of peanuts against Aspergillus and/or Alternaria.

Another embodiment of the invention provides methods of inhibiting the growth of fungi, particularly Aspergillus and Alternaria, by applying the biocontrol strain of the present invention to an environment in which the plant pathogenic fungus may grow. This includes application to the plant, a plant part, or seeds of the plant (prior to planting). Alternatively, the strain could be applied to the soil in which the plant to be protected is growing or will grow. As noted above, the rate of application will vary depending on various factors.

The biocontrol strains of the present invention may be used in any manner known in the art, including coating seeds with an effective amount of the biocontrol agent, or in furrow application of the biocontrol agent directly into the soil and foliar application. Such methods are well known in the art and are described, for example, in the published European Application EP 0 472 494 A2. Furthermore, the strains can be mixed in formulation with known pesticides in a manner described in the art.

The following examples are offered by way of illustration and not by way of limitation.

EXPERIMENTAL
Mutagenesis and Selection of Strain AU634

A strain of *Bacillus thuringiensis* (HD-548) with lepidopteran activity was selected for high chitinase activity using an in vitro assay. Incubation of this strain with N-methyl-N'-nitro-N-nitrosoguanidine resulted in several colonies exhibiting clearing zones after 24 hr. when plated on nutrient agar containing 0.4% chitin. One colony was selected and subsequently designated (AU634) and assayed in vitro for fungicidal activity against *Aspergillus flavus* and

*Alternaria solani*. In both cases, AU634 inhibited growth of the fungi, whereas HD-548 did not. In peanut field trials, initial seed treatments, with one subsequent soil drench at pegging, using AU634 significantly reduced Aspergillus spp. fungal colonization and aflatoxin concentration of the harvested peanuts when compared to the untreated control. Results of glasshouse assays of peanuts grown in pots demonstrate that AU634 (used as a seed treatment and soil drench) also significantly reduced plant damage due to the lesser cornstalk borer, *Elasmopalpus lignosellus*. This soil insect causes direct damage to the peanut peg and pod which also allows easier penetration by Aspergillus. This insect has also been shown to vector *Aspergillus conidia*.

Isolation of Chitinase

Methods for the isolation of proteins are available in the art. See for example *Current Protocols in Molecular Biology*, Vols. 1 and 2, Ausubel et al. (eds.), John Wiley & Sons, NY (1988). Additionally, antibodies can be prepared against substantially pure preparations of the protein. See, for example, Radka et al. (1983) *J. Immunol.* 128:2804; and Radka et al. (1984) *Immunogenetics* 19:63. Any combination of methods may be utilized to purify the chitinase protein. As the protocol is being formulated, chitinase activity is determined after each purification step.

Generally, chitinolytic activity from *Bacillus thuringiensis* HD-AU634 strain was initially detected on nutrient agar+0.4% colloidal chitin. HD-AU634 was plated on two (2) agar plates; one was placed at room temperature, and the other was placed at 30EC. Strong chitinolytic activity was detected at day 6 for plate incubated at 30EC; at day 8, the plate showed almost complete clearing around the colonies. The plate that was left at room temperature showed weak chitinolytic activity at day 8. Thus from these preliminary results, the HD-AU634 was grown in 1 of nutrient broth+ 0.4% colloidal chitin at 30EC, 250 rpm for 7–10 days before they were harvested. A 7-day old culture has about 75% spores, and 25% cells (rod shape with spores inside) as observed under the light microscope. After 10–11 days, there was about 99% spores observed.

The above culture was centrifuged at 10,000 rpm, 4EC, for 40–45 minutes. The supernatant was collected (a small sample was saved for activity+protein concentrate assays), and concentrated 10×, using a 10K ultrafiltration membrane, 60 psi compressed nitrogen, at 4EC. The concentrated supernatant (save a small sample for activity+protein concentrate assays) was then precipitated with 30% ammonium sulfate (keep supernatant on crushed ice, stir, and add ammonium sulfate slowly to avoid local high concentrate effect). The sample was centrifuged at 10,000 rpm for 30 minutes, or 15,000 rpm for 20 minutes, 4EC. The pellet at this stage is known as P30. The remaining supernatant was collected and continued up to 70% ammonium sulfate addition. Again, the sample was centrifuged, and the pellet (known as P70) now contains the majority of chitinase activity. The P70 is now dissolved in 5–10 ml of sodium phosphate buffer (pH 7.0, 0.02M) and dialyzed against the same buffer overnight (3×1.5 L, 4EC), using a 6–8000 MW membrane. The dialyzed sample was then lyophilized and stored at -20EC. The ammonium sulfate can also be removed by passing the dissolved P70 through a G-2 Sephadex Column.

Chitinase Activity Assay

The chitinolytic activity was measured according to Nelson-Somogyi's Reducing Sugar Method (*Methods in Enzymology*. Vol. VIII, pp. 3–26). The reaction mixture was prepared as follows:
Sample Mixture
0.5 ml chitin (20 mg\ml)
0.5 ml buffer, sodium phosphate, 0.1M, pH 7.0
0.5 ml enzyme solution
1.5 ml distilled water
30 Fl PMSF, 0.1M
Control
0.5 ml chitin (20 mg\ml)
0.5 ml buffer, sodium phosphate, 0.1M, pH 7.0
2.0 ml distilled water
30 ul PMSF, 0.1M The prepared sample mixture was vortexed. 0.7 ml was removed (T=0), and centrifuged at 12K rpm, 3–4 minutes. After this, 0.5 ml of the clear supernatant was collected for determination of reducing sugar. The original sample mixture was incubated in a water bath at 45–50EC for 90 minutes with intermittent shaking. After 90 minutes, a small sample was removed for determination of reducing sugar as described above. The O.D. reading can be converted into amount of reducing sugar by using the NAG standard curve. The enzyme activity was calculated by taking the reducing sugar after the reaction minus the reducing sugar before the reaction divided per time. The specific activity can be calculated by dividing enzyme activity per mg of protein (determined from Lowry Protein Assay Kit, Sigma). The preliminary results indicated that the enzyme activity of P70 was approximately 1.014 Fmole of reducing sugar\minute.

HPLC Ion-exchange, Analytical Scale

The P70 proteins, which were stored at -20EC, were dissolved in distilled water (approximately 5–10 mg\ml), and filtered through a 0.22 Fm filter paper. The filtered sample was then loaded on the ion-exchange column, Protein Pak DEAE 5PW, with Tris (0.05M, pH 7.5), and Tris (0.05M)—NaCl(0.5M), pH 7.5 buffers. The fractions were collected and their chitinolytic activity were measured. Highest activity was determined in the first peak (0–5.88 minutes). This initial clean-up step allowed the unbound chitinase to be removed from other protein impurities.

The above step was repeated several times, and the first fractions were pooled, washed with cold Tris buffer (0.05M, pH 85), and concentrated through 10K membrane. A small sample was ran on SDS-PAGE (Phastsystem). There were three (3) major (50, 40, 21 KDas), and one minor (10 KDa) protein bands. The original sample was loaded on HPLC ion-exchange, using Tris (0.05M, pH 8.5), and Tris (0.05M)—NaCl (0.5M), pH 8.5.

Three (3) fractions were collected and washed with sodium phosphate (0.05M, pH 7.0), and concentrated through 10K membrane. Highest activity was observed in the third fraction (14.72–29.32 minutes elution time). A small sample of this fraction was loaded on SDS-PAGE, and it showed that there were only two (2) protein bands with MW of 40, and 50 Kdas.

It was not possible to separate these two (2) proteins using gel filtration. It is possible that these two (2) protein bands belongs to the overall chitinase, since DTT was used in the sample buffer of SDS-PAGE.

HPLC Ion-exchange, Preparative Scale

Protein Pak DEAE 5PW, columns #8 and #4 were used in the preparative HPLC ion-exchange runs at pH 7.5 and 8.5 respectively. Same types of buffers and concentration were used as in the analytical scale for pH 7.5, and pH 8.5 runs respectively. In the pH 7.5 run, the first two (2) peaks were collected at 6.69–15.35 minutes (#1), 15.36–22.33 minutes (#2).

These two (2) fractions were pooled, washed with cold sodium phosphate buffer (0.05M, pH 7.0), concentrated through 20K membrane, and loaded on SDS-PAGE. The first fraction contained a higher amount of the two (2) putative chitinase bands at 40 and 50 Kdas. This fraction was reloaded on ion-exchange, pH 8.5, preparation scale, and collected a multi-peak at 24–38 minutes.

HPLC Gel Filtration

This multi-peak was pooled, and washed with cold sodium phosphate buffer (0.05M, pH 7.0). The fraction was run on gel filtration, Protein Pak 125, with sodium phosphate buffer (0.05M, pH 7.0), and flow rate of 0.5 ml\minute for 90 minutes. Only one major broad peak was found between 16–24 minutes. The fraction was collected and lyophilized. A small sample of this lyophilized protein was loaded on SDS-PAGE, which showed six (6) protein bands: 21, 25, 40, 50, 70, and 116 Kdas. In fact, these protein bands were not different from the proteins collected after prep. ion-exchange, pH 8.5 run, and its subsequent gel filtration run. The major problem encountered in the prep. column (pH 8.5) was that there were about five (5) peaks that were very close to each other, and hence it was difficult to isolate the individual peaks.

Isolation of the Chitinase Gene from *Bacillus thuringiensis* strain AU634 and Determination of its Role in the Control of Aspergillus-like Fungi and the Reduction in Aflatoxin Concentrations Total genomic DNA from Bt strain AU634 is isolated as described by Kronstad (1983). Southern blot hybridizations will be performed with AU634 digested with BamHI using a $P^{32}$-labeled oligonucleotide corresponding to the first eight (8) amino acids obtained from the N-terminal protein sequence. The corresponding DNA fragment size will be excised from the agarose gel, and BamHI and Sau3A libraries will be prepared using the BamnHI site of pUC18/19 or pBluescriptKS (Stragene, La Jolla, Calif.). This library will be screened again using a oligonucleotide probe for chitinase expression as described by Watanabe et al. (1990) J. Biol. Chem. 265:15659–15665. Putative clones will be sequenced using the method of Sanger et al. (1977) Proc. Natl. Acad. Sci. USA 74:5463–5467, using both commercial primers as well as the oligonucleotide corresponding to the N-terminus of the protein (SEQ ID NO: 1). Additionally, clones can also be screened on LB agar plates supplemented with 0.4% chitin and 50 Fg/ml ampicillin.

To enhance the expression and accumulation of the chitinase in *E. coli*, the gene will be inserted directly downstream of the orf-1 and orf-2 polycistron in pIGE-4. This vector has been shown to enhance expression and accumulation levels of foreign genes. Chitinase expression and chitinolytic activity will be assayed using the 4-methylumbelliferyl N, N'diacetylchitobiose procedure described by Robbins et al. (1988) J. Biol. Chem. 263:443–447. The biological activity of purified chitinase against Aspergillus spp. will be performed against various fungi using both in vitro bioassays (agar plates) and evaluation of the zones of inhibition.

Evaluate Colonization by Bacillus spp. on Roots, Crowns, Branches, and Pegs of Developing Peanut Plants Spontaneous mutants of rifampicin-resistant isolates of HD-548 and AU634 have been selected (Mickler et al., (1995) Plant and Soil 175:291–299). Using these strains, it will be possible to sample tissue from treated plants in growing in fields or the greenhouse to determine colonization by our bacterial isolates. Seed will be treated with endospores of rifampicin-resistant isolates. Two (2) or three (3) peanut plants will be collected from field trials at regular intervals during the growing season (at least monthly starting in July). These plants will be put on ice and returned to the laboratory. Excess soil will be removed by vigorous shaking and plant tissue air-dried at room temperature for several days. Samples will be made of roots, crown regions of plants, branches, and developing pegs and pods. One gram (dry weight) of each sample will be homogenized with 100 ml water and filtered in sterile system. These suspensions will be diluted in 10-fold series, and 0.1-ml aliquots will be spread on a semiselective media for Bacillus spp. that also contains rifampicin (Turner and Backman, (1991) Plant Dis. 347–353). Colonies of Bacillus isolates will be enumerated after incubation at 30EC for 48 hours. Colonization levels of $10^3$ to $10^6$ colony-forming units on root, peg, and pod tissue of treated plants are expected. A negative relationship between colonization and the incidence of *A. flavus*-type fungal invasion at any particular sampling date is also expected.

Determine Possible Effects on Plants When Plants are Treated with Selected Bacillus Isolates. Possible Effects Include Growth Promotion and Induced Systemic Resistance Field trials will be established with peanut plants treated with each Bacillus isolate. Applications will be made as described in previous work (Mickler et al., (1995) Plant and Soil 175:291–299), or with minor modifications for treating large field areas. Beginning at emergence, plants treated with each isolate and untreated plants will be sampled on two week intervals. These plants will be returned to the laboratory, and carefully measured. Measurements will be made on whole plant and root weight, number of branches, and precise developmental state. In addition, defoliation due to leaf spot will be assessed on sampled plants for determination of possible induced systemic resistance due to the introduced Bacillus. Other diseases, such as southern stem rot, limb rot, etc., will be assessed.

Evaluate Colonization by Bacillus spp. on Developing Corn Plants and Determine Possible Effects on Plants When Treated with Selected Bacillus Isolates Following the examples set forth above for peanuts, the colonization and effects of the Bacillus isolates on corn will be tested.

The use of biological control methods in plant production systems is rapidly becoming common practice. These methods include means by which to alleviate plant stress by providing protection from seedling diseases such as root rots. Most of these methods have limited application, such as the parasitic wasps that selectively attack only single species. All of these biological control options are beneficial due to their minimum impact on the environment. Biocontrol products used in plant protection have been commercialized that are applied as seed treatments. As such, they change microbiology of the soil at the soil-root interface. Studies on the effects of such potential biocontrol products on the ecology of native soil organisms are needed.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A biocontrol strain of the *Bacillus thuringiensis* designated AU634 and deposited as NRRL B-21620.

2. A method for controlling or inhibiting the growth of a plant pathogenic fungus by applying an effective amount of a biocontrol strain AU634 to an environment in which the plant pathogenic fungus may grow.

3. The method of claim 2, wherein said fungus is selected from the group consisting of Botrytis, Alternaria, and Aspergillus.

4. The method of claim 3, wherein said fungus is Botrytis.

5. The method of claim 4, wherein said Botrytis is *Botrytis cinerea*.

6. The method of claim 3, wherein said fungus is Alternaria.

7. The method of claim 6, wherein said Alternaria is *Alternaria solani*.

8. The method of claim 3, wherein said fungus is Aspergillus.

9. The method of claim 8, wherein said Aspergillus is *Aspergillus flavus*.

10. The method of claim 8, wherein said Aspergillus is *Aspergillus parasiticus*.

11. A method for controlling or inhibiting the growth of a plant pathogenic fungus by applying an effective amount of biocontrol strain AU634 to a plant or plant part in order to protect said plant or plant part from said plant pathogenic fungus.

12. A method for controlling or inhibiting the growth of a plant pathogenic fungus by applying an effective amount of biocontrol strain AU634 to seed in order to protect a plant which develops from said seed from a plant pathogenic fungus.

13. The method of claim 12, wherein said plant pathogenic fungus is selected from the group consisting of Botrytis, Alternaria, and Aspergillus.

14. The method of claim 13, wherein said fungus is Aspergillus.

15. The method of claim 14, wherein said Aspergillus is *Aspergillus flavus*.

16. The method of claim 14, wherein said Aspergillus is *Aspergillus parasiticus*.

17. The method of claim 13, wherein said fungus is Botrytis.

18. The method of claim 17, wherein said Botrytis is *Botrytis cinerea*.

19. The method of claim 13, wherein said fungus is Alternaria.

20. The method of claim 19, wherein said Alternaria is *Alternaria solani*.

21. The Bt strain of claim 1, which has been transformed with a heterologous gene.

22. The strain of claim 21, wherein said heterologous gene is an insecticidal gene.

23. The strain of claim 21, wherein said heterologous gene is a fungicidal gene.

* * * * *